(12) United States Patent
Urano

(10) Patent No.: US 7,342,652 B2
(45) Date of Patent: Mar. 11, 2008

(54) BIOMEDICAL OPTICAL DEVICE AND BIOMEDICAL OPTICAL MEASURING METHOD

(75) Inventor: Taeko Urano, Kawasaki (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 222 days.

(21) Appl. No.: 11/333,523

(22) Filed: Jan. 17, 2006

(65) Prior Publication Data

US 2006/0184050 A1 Aug. 17, 2006

(30) Foreign Application Priority Data

Jan. 18, 2005 (JP) ............................. 2005-010700

(51) Int. Cl.
*G01N 33/48* (2006.01)
(52) U.S. Cl. ........................................ 356/39; 356/40
(58) Field of Classification Search .................... None
See application file for complete search history.

(56) References Cited

U.S. PATENT DOCUMENTS

2003/0002028 A1* 1/2003 Rice et al. ..................... 356/39
2007/0158585 A1* 7/2007 Hall et al. ................ 250/458.1

FOREIGN PATENT DOCUMENTS

JP 2000-237195 9/2000

OTHER PUBLICATIONS

Shechao Feng, et al., Photon Migration in the Presence of a Single Defect: A Perturbation Analysis, Applied Optics, vol. 34, No. 19, pp. 3826-3837, Jul. 1, 1995.
Motoki Oda, et al., Nearinfrared Time-Resolved Spectroscopy System for Tissue Oxygenation Monitor, Proc. SPIE vol. 4160, pp. 204-210, 2000, Japan.

* cited by examiner

*Primary Examiner*—Michael P. Stafira
(74) *Attorney, Agent, or Firm*—Amin, Turocy & Calvin, LLP

(57) ABSTRACT

Light having a wavelength to be absorbed by a target object is irradiated from a light irradiating unit toward a subject while varying its intensity in the course of time. At least two detecting elements arrayed along a scanning direction detect a component having a large time delay out of the light propagated through the subject, for example, as departing from the light irradiating unit. By comparing measured data on the basis of the light detected by the at least two detecting elements with measured data in the case where the target object is not present in a light irradiation region, the depth of the target object at a location of the light irradiating unit is acquired.

17 Claims, 6 Drawing Sheets

BIOMEDICAL OPTICAL DEVICE AND BIOMEDICAL OPTICAL MEASURING METHOD

CROSS-REFERENCE TO RELATED APPLICATIONS

This application is based upon and claims the benefit of priority from prior Japanese Patent Application No. 2005-010700, filed Jan. 18, 2005, the entire contents of which are incorporated herein by reference.

BACKGROUND OF THE INVENTION

1. Field of the Invention

The invention relates to a biomedical optical device and a biomedical optical measuring method for use in measurement of biomedical internal information using light noninvasively.

2. Description of the Related Art

Various diagnostic techniques are known for examining the inside of a body. One of them is optical measurement, which is advantageous in that a compound to be measured can be selected by tuning a wavelength without any problem of radiation exposure. The device can be also reduced in size and lowered in cost, and it is being developed into products for home use or non-clinical use, while other diagnostic devices are mainly designed for clinical and professional use.

Biomedical information measuring devices making use of optical measurement (hereinafter, referred to as biomedical optical devices) are already manufactured in certain commercial products such as sphygmograph (pulse oximeter) or Optical Topography (registered trademark). The latter is to monitor the consumption trend of oxygen, and its subject is mapping of time course of hemoglobin and myoglobin in brain and muscle. Formerly, a handy oxygen monitor was distributed, and it is no longer manufactured at the present.

As compared with the existing established diagnostic devices, such as an X-ray diagnostic apparatus, an X-ray CT apparatus, a magnetic resonance imaging (MRI) apparatus, an ultrasound echo, and a nuclear medicine (positron) diagnostic device, the market scale of optical biomedical measuring devices is smaller. The technology of biomedical optics itself has been known for 30 years, and has attracted wide attention several times in the past. In spite of the biomedical "boom" both inside and outside Japan at the present, corresponding market for products is not formed yet.

A configuration of a conventional biomedical optical device is explained. For example, in a general biomedical optical device, as disclosed in Jpn. Pat. Appln. KOKAI Publication No. 2000-237195, an optical probe is pressed to the skin surface of a body, detection light is irradiated into the body through the skin, transmitted or reflected light is transmitted again through the skin, the exit light is measured, and various items of biomedical information are calculated. From the measured light, the position and depth of measurement are analyzed. This analytical technique includes a technique of adjusting a distance (abbreviated to be R) between a light source and a detector (spatial resolution method), and a technique of obtaining depth information from difference in light arrival time using a light source changing in intensity in the time course (time resolution method).

The former spatial resolution method is disclosed in, for example, Appl. Opt. Vol. 34, p. 3826, 1995, which is based on the idea that information from a deep position can be obtained when R is larger, using light of a light source continuous in time as incident light. For example, using one light source and two detecting elements, information of a shallow part and a deep part is obtained from signals corresponding to each R. Concerning R, depth information of up to 0.35R can be obtained, and the position reaching this depth is the middle point of R. On the other hand, the latter time resolution method requires a light source of narrow time width and a detecting element of fast time response, in order to correspond to depth information by dividing the time response of an optical signal.

However, the conventional biomedical optical device involves, for example, the following problems.

Firstly, signal quality fluctuates depending on a measuring state. That is, in the contact state with the body in the conventional biomedical optical device, intensity or property of the optical signal varies significantly when measuring the light, depending on the contact state of a probe for irradiating light or a probe for detecting the exit light with the skin, or distance or angle. Therefore, depending on whether or not the probe is contacting with the skin, whether or not an air layer exists between the probe and the akin, the signal form may be distorted, and the obtained signal may vary in quality.

Secondly, a measuring range is limited by the method of detection. More specifically, in the case of using the spatial resolution method, a large R is needed when attempted to obtain information of a deep position. For example, information at depth of 5 cm corresponds to R of 15 cm. However, since the human body is made of curves, a position 15 cm apart straightly in distance is away from the skin. On the curve obtained by analysis, a corresponding position on the skin cannot be determined automatically, and there is a limit in analysis of measuring position and depth from the obtained light. The spatial resolution method is effective when acquiring information of two overlaid layers, for example, when distinguishing the skin and the subcutaneous fat, or distinguishing the cranial bones and the cerebral cortex. However, when the thickness of the upper layer is unknown or differs depending on location, trial and error may be needed to set the value of R.

Thirdly, there are limits in the aspects of security and price. That is, in the time resolution method, a light source of narrow time width and a detecting element of fast response are needed, but such a device is expensive, and requires high voltage for driving. For this reason, it is dangerous when brought closer to the skin.

In the conventional devices, therefore, it has been difficult to analyze the measuring position and depth from the measured light, and signals of high quality enough for analysis cannot be acquired, while assuring high safety, if attempted to compose a more inexpensive device than other diagnostic apparatuses.

BRIEF SUMMARY OF THE INVENTION

The invention has been devised in the light of the above background, and it is an object of the invention to provide a biomedical optical device and a biomedical optical measuring method capable of analyzing measuring position and depth using light free from exposure risk, and also capable of acquiring signals of high quality enough for analysis while assuring high safety, if attempted to compose a more inexpensive device than other diagnostic apparatuses.

According to an aspect of the present invention, there is provided a biomedical optical device which comprises: a light irradiating unit which is arranged on a surface of a subject, and configure to irradiate light toward a region to be irradiated in the subject, the light with a wavelength to be absorbed by a target object in the subject and intensity varied in time; at least two detecting elements which are arrayed at different distances from a location of the light irradiating unit, and which detect the light propagated through the subject; a storage unit configure to store the intensity of light detected by each of the detecting elements when the target object is not present in the region to be irradiated; a calculating unit which specifies the detecting element detecting the light which was reflected by the target object or propagated through the target object, by comparing the intensity of light detected by each of the detecting elements when the stored target object is not present in the region to be irradiated with the intensity of light detected by each of the detecting elements when the target object is present in the region to be irradiated, and which calculates the depth of the target object by reference to the location of the light irradiating unit on the basis of the distance between the specified detecting element and the light irradiating unit; and an output unit which outputs the calculated depth of the target object.

According to another aspect of the present invention, there is provided a biomedical optical measuring method which comprises: irradiating light toward a region to be irradiated in a subject by a light irradiating unit arranged on the surface of the subject, the light with a wavelength to be absorbed by a target object in the subject and intensity varied in time; detecting the light propagated through the subject by at least two detecting elements which are arrayed at different distances from a location of the light irradiating unit; specifying the detecting element detected the light reflected by the target object or propagated through the target object by comparing the intensity of light detected by each of the detecting elements when the stored target object is not present in the region to be irradiated with the intensity of light detected by each of the detecting elements when the target object is present in the region to be irradiated; calculating the depth of the target object by reference to the location of the light irradiating unit on the basis of the distance between the specified detecting element and the light irradiating unit; and outputting the calculated depth of the target object.

According to yet another aspect of the present invention, there is provided a biomedical optical measuring method which comprises: irradiating light toward a region to be irradiated in a subject by a light irradiating unit arranged on the surface of the subject, the light having a wavelength to be absorbed by a target object in the subject and intensity varied in time; detecting the light propagated through the subject by at least two detecting elements which are arrayed at different distances from the location of the light irradiating unit; specifying the detecting element detected the light reflected by the target object or propagated through the target object by comparing the intensity of light detected by each of the detecting elements when the stored target object is not present in the region to be irradiated with the intensity of light detected by each of the detecting elements when the target object is present in the region to be irradiated; calculating the depth of the target object by reference to the location of the light irradiating unit on the basis of the distance between the specified detecting element and the light irradiating unit; repeating irradiation of the light toward the region to be irradiated, detection of the light propagated through the subject, and calculation of the depth of the target object while moving the light irradiating unit to at least two positions along substantially one direction on the surface of the subject, thereby acquiring the depth of the target object at each of the at least two positions; and obtaining a tomographic image concerning the target object on the basis of the acquired depth of the target object at each of the at least two positions.

DETAILED DESCRIPTION OF THE INVENTION

An embodiment of the invention will be described below with reference to the accompanying drawings. In the following explanation, substituent elements having same function or configuration are identified with same reference numbers, and duplicate explanation is give only when necessary.

Figure 1:
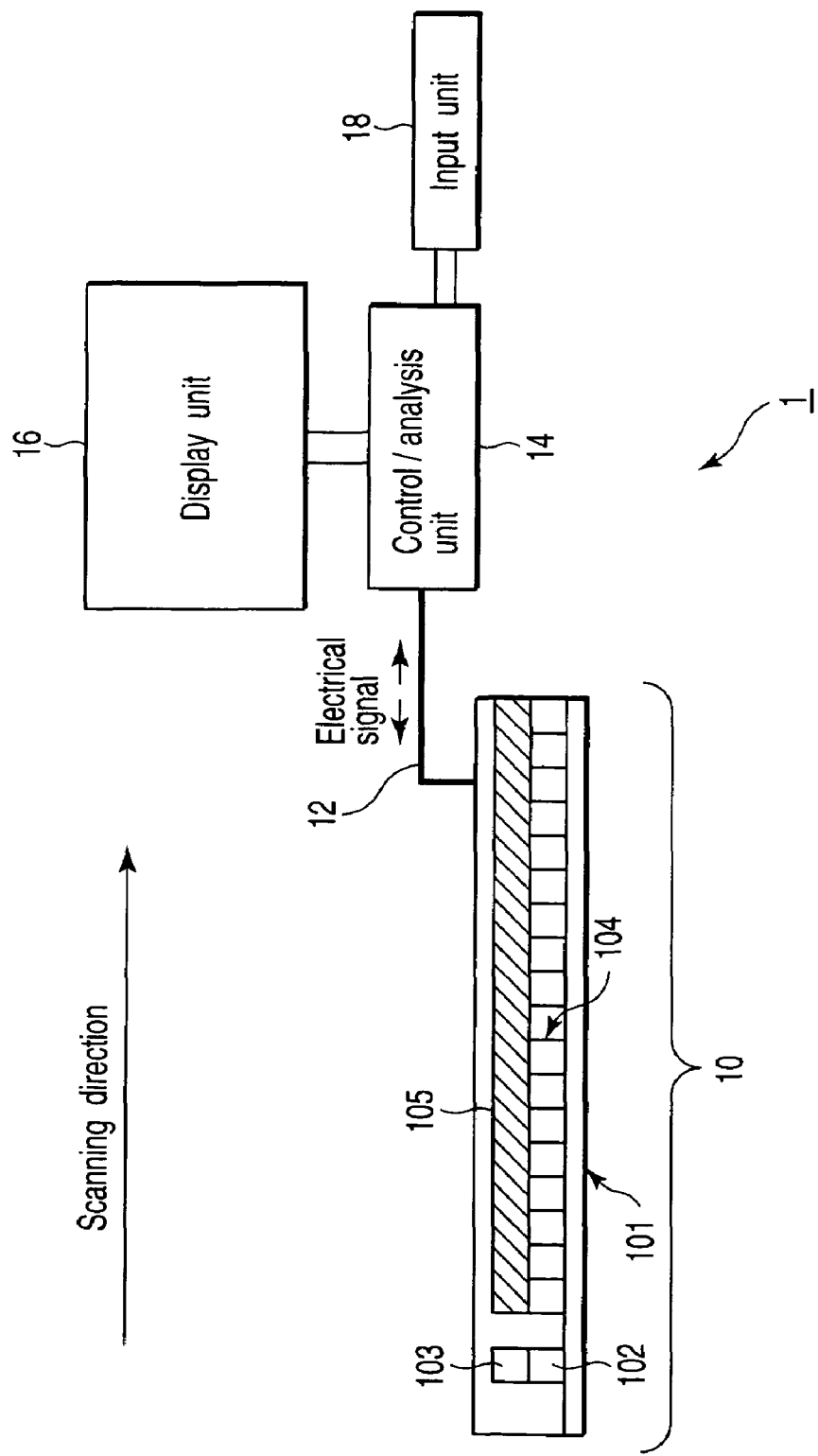
FIG. 1 is a block diagram showing a configuration of a biomedical optical device 1 according to an embodiment of the invention.

FIG. 1 is a block diagram showing a configuration of a biomedical optical device 1 according to an embodiment of the invention. As shown in FIG. 1, the biomedical optical device 1 comprises a probe 10, an electrical signal transmitter 12, a control/analysis unit 14, a display unit 16, and an input unit 18.

The probe 10 irradiates light into the body under the control of the control/analysis unit 14, and executes optical scanning for detecting the exit light from the body. The probe 10 includes a matching membrane 101, a light irradiating unit 102, a drive circuit 103, a detecting element 104, and a signal processing circuit 105.

The matching membrane 101 forms a contact surface of the biomedical optical device 1 with the skin. The matching membrane 101 plays a role of a light matching layer for preventing light scattering and also plays a role of a buffer material for preventing denting into the skin when touching the device 1 (deformation of the skin surface or subcutaneous tissues). Its material may be a silicone resin thin plate or the like.

The light irradiating unit 102 is a laser diode for generating light for measurement on the basis of a drive signal from the drive circuit 103, especially light changing in intensity in a predetermined period T in optical measurement described below. A wavelength of light irradiated from the light irradiating unit 102 is in a spectrum of absorption of a target object (for example, blood (hemoglobin), bone (calcium), fat, muscle (myoglobin), etc.). The period T is determined, for example, from the anatomical viewpoint, and for example, a half-period T/2 (or a full width at half maximum of light intensity varying with time) is preferred to be 5 nanoseconds or less.

The drive circuit 103 generates a drive signal varying in the predetermined period T under the control of the control/analysis unit 14, and supplies the drive signal to the light irradiating unit 102.

The detecting element 104 detects light propagated through the body, and converts the light into an electrical signal. At least two detecting elements 104 are disposed at different positions from the light irradiating unit 102. In this embodiment, photo diodes are used as the detecting elements, but other detecting elements may be also used such as a CCD, a photomultiplier and others having a photoelectric converting function.

The probe 10 may be composed in various configurations, such as at least two detecting elements 104 arrayed at different distances from the light irradiating unit 102 along one direction, at least two detecting elements 104 arrayed at different distances from the light irradiating unit 102 at least along one direction, at least two detecting elements 104 arrayed on a two-dimensional matrix along the detection object surface, and at least two detecting elements 104 arrayed three-dimensionally so as to be away from the detection object surface and the at least two detecting elements 104. For the sake of simplicity of explanation, the embodiment employs a one-dimensional array type probe 10 having at least two detecting elements 104 arrayed at different distances from the light irradiating unit 102 along one direction (scanning direction).

A series of processes, in which light is irradiated from the light irradiating unit 102 in the period T and light of maximum intensity in one period is detected by each of the detecting elements 104 at a predetermined time width, is called one scan.

The signal processing circuit 105 changes over a detecting element 104 (or at least two detecting elements) to be selected at a predetermined time width on the basis of a control signal from the analysis/control unit 14, and sends out only an electrical signal from the selected detecting element to the electrical signal transmitter 12.

The electrical signal transmitter 12 transmits the control signal from the control/analysis unit 14 to the probe 10, and transmits a signal based on the light detected by the probe 10 to the control/analysis unit 14.

The control/analysis unit 14 controls the operation of the probe 10, analyzes the signal based on the light detected by the probe 10, and generates predetermined biomedical information.

Figure 2:
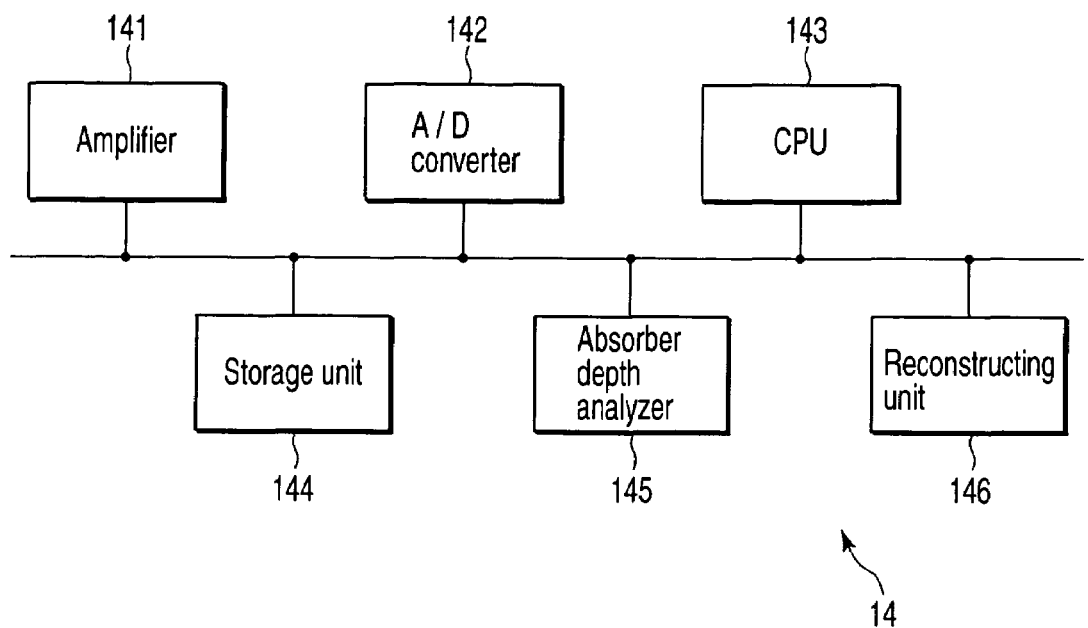
FIG. 2 is a block diagram showing a configuration of a control/analysis unit 14.

FIG. 2 is a block diagram showing a configuration of the control/analysis unit 14. As shown in FIG. 2, the control/analysis unit 14 includes an amplifier 141, an A/D converter 142, a CPU 143, a storage unit 144, an absorber depth analyzer 145, and a reconstructing unit 146.

The amplifier 141 amplifies a signal from each detecting element 104.

The A/D converter 142 converts an analog signal from the amplifier 141 into a digital signal. The amplifier 141 and A/D converter 142 may be also provided in the signal processing circuit 105.

The CPU 143 controls the biomedical optical device 1 dynamically or statically. In particular, the CPU 143 control the drive circuit 103 so that the light is irradiated from the light irradiating unit 102 at a predetermined timing, wavelength, intensity, and repetition period T. The CPU 143 changes over a detecting element 104 to be selected along the scanning direction at a predetermined time width, and controls the signal processing circuit 105 so as to send out only the electrical signal from the selected detecting element to the electrical signal transmitter 12.

The storage unit 144 stores an electrical signal based on measured light at each detection position. The storage unit 144 also stores the light intensity detected by each detecting element in each target object (at each wavelength of irradiated light) if there is no target object (light absorber) acquired preliminarily.

The absorber depth analyzer 145 receives a digital signal from the A/D converter 142, and analyzes the subcutaneous depth of the target object on the basis of the received signal and data stored in the storage unit 144. That is, the absorber depth analyzer 145 compares the light intensity detected by each detecting element in actual measurement with the light intensity detected by each detecting element in the absence of the target object (light absorber), and analyzes the position (depth) of the target object. This analysis is executed once in every one optical scanning.

The reconstructing unit 146 reconstructs a tomographic image of a measuring region on the basis of the depth of the target object obtained in the absorber depth analyzer 145.

The display unit 16 displays the biomedical information received from the control/analysis unit 14 in a predetermined format.

The input unit 18 has switches for receiving various instructions, commands and information from the operator.

Figure 3:
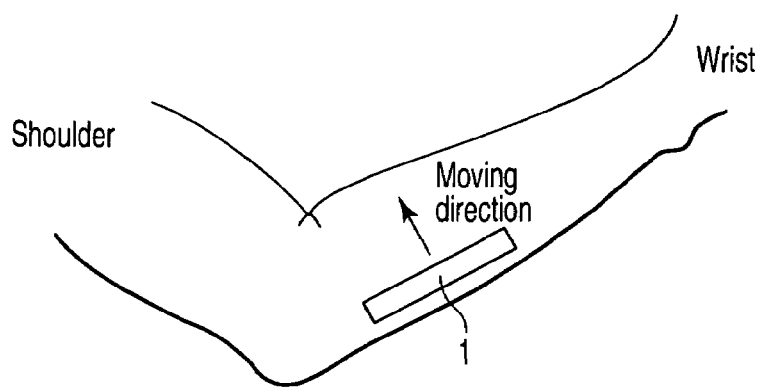
FIG. 3 is a view showing an example of a mode of use of the biomedical optical device 1.

The biomedical optical device 1 is mounted on the subject, for example, as shown in FIG. 3 such that a direction from the wrist to the elbow coincides with a scanning direction, and the device 1 is used by moving in a direction (moving direction) vertical to the scanning direction.

Note that the configuration of the biomedical optical device 1 is not limited as above description and can be modified if necessary. Specifically, a device for improving light-detecting efficiency (for example, photomultiplier or the like) may be arranged between the matching membrane 101 and the detecting element 104.

(Measuring Method of Biomedical Optical Device)

A technique of optical measurement to be executed by the biomedical optical device 1 will be explained.

Figure 4:
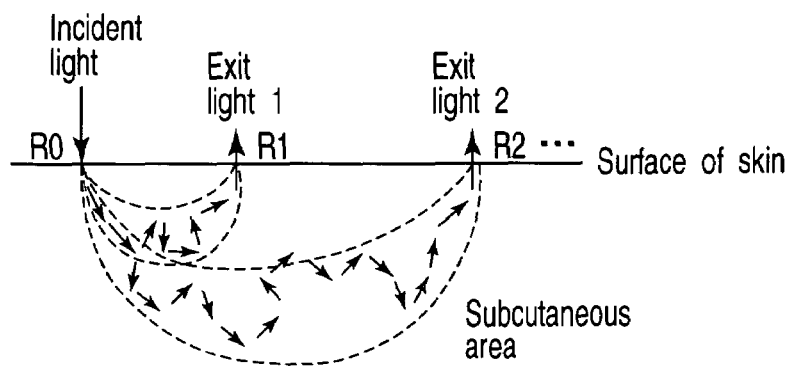
FIG. 4 is a view showing a mode of scatter of light entering in the skin and exiting from the skin.

Generally, the human body is a medium which scatters light intensively. Therefore, as shown in FIG. 4, when the light entering from the skin penetrates into a deeper position than the corium, the light scatters many times until coming out from the skin, and exit lights are isotropic. In this case, the average of distances along the actual light transmitting routes is said to be not less than five times of two times of the reached depth (running distance of one normal reflection of light). For example, when desired to obtain information at a position of 10 mm beneath the skin, light scatters repeatedly and comes out after running a distance of 100 mm or more, and thus, time lag is 0.3 nanoseconds or more. Hence, depending on the resolution in the depth direction, the required time width of incident light and response speed of the detector vary. By making use of this phenomenon, this technique is intended to acquire the sectional shape of the absorber by executing optical measurement by use of the light source for irradiating light changing in intensity in the time course and the detector, and by calculating the depth and position of the absorber from the comparison of the spatial distribution of measured light intensity with reference data.

Figure 5:
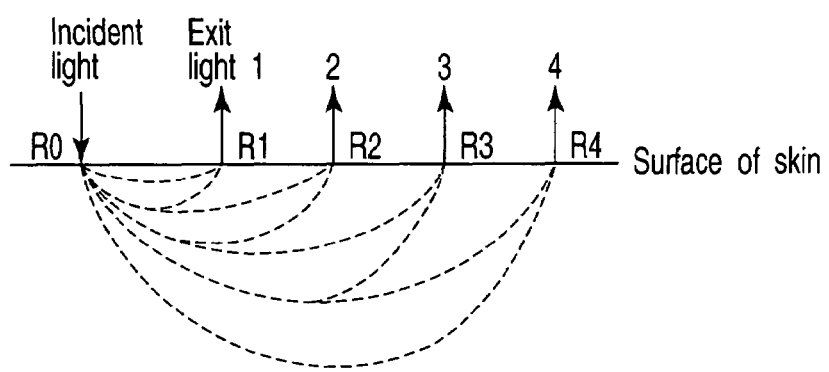
FIG. 5 is a conceptual view showing a mode of light entering in the skin at position $R_0$ and leaving from positions $R_1$ to $R_n$ after propagating through the body.
Figure 6:
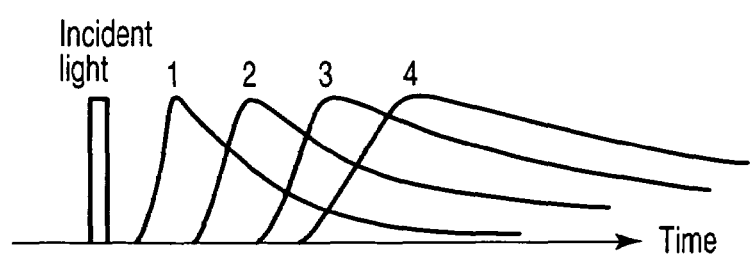
FIG. 6 is a view showing time course of light intensity (response curve) detected at the positions $R_1$ to $R_n$.

FIG. 5 is a conceptual view showing a feature of light entering in the skin at light source position $R_0$ and exiting from positions $R_1$ to $R_n$ after propagating through the body. FIG. 6 is a view showing time-curse of light intensity (response curve) detected at the positions $R_1$ to $R_n$ by numbering the detecting elements from the close to the light source position $R_0$ of the device 1 (the position of the light entering in the skin) in straight distance up to the n-th detecting element $R_n$.

Figure 7:
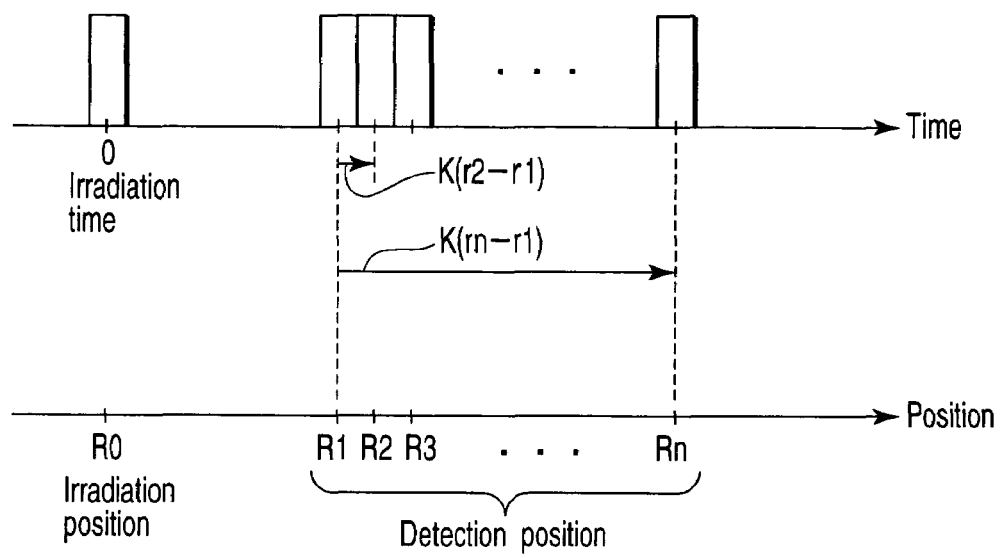
FIG. 7 is a view showing an example of gate driving timing of each detecting element depending on the position.

For example, the detecting element $R_1$ closest to the light source in straight distance is set at a position within 5 mm from the light source position $R_0$ of the light entering in the skin, and the time until a signal is detected by this detecting element is supposed to be reference time t. Supposing the distance between the n-th detecting element and the position $R_0$ to be $r_n$, an initial value of a time delay until the signal is detected by this detector is set as $k\times(r_n-r_1)$ (k: constant). On the basis of this value, as shown in FIG. 7, the detecting element is selected using the time width calculated from the spatial resolution, and only the electrical signal is acquired from the selected detecting element, and the depth of the target object is analyzed.

Therefore, by delaying the detection timing of each detecting element depending on each distance between the light irradiating unit 102 and each of at least two detecting elements 104, the detection timing of each detecting element (timing of signal uptake gate) is controlled so that each detecting element detects a light component with a large time delay is moving away from the light irradiating unit 102. For example, the detecting element at the position $R_0$ is driven at a time difference (delay) of $k\times(r_2-r_1)$ from the time of light irradiation, and electrical signals based on lights detected at each timing plot a response curve as shown in, for example, FIG. 6.

A wavelength of light for use in irradiation is selected to coincide with absorption of a compound contained in the subcutaneous tissue desired to be measured. For example, when desired to measure the position of the blood vessel, a near infrared wavelength of strong absorption of hemoglobin as the blood component is selected, while wavelengths close to absorption of melanins contained in the skin or water are avoided because the light is damped. Besides, since the intensity of light scatter is inversely proportional to the fourth power of measuring wavelength, damping by scatter must be also taken into consideration. The contrast can be enhanced by selecting compounds much contained in the desired subcutaneous tissues, and not contained in peripheral tissues.

Figure 8:
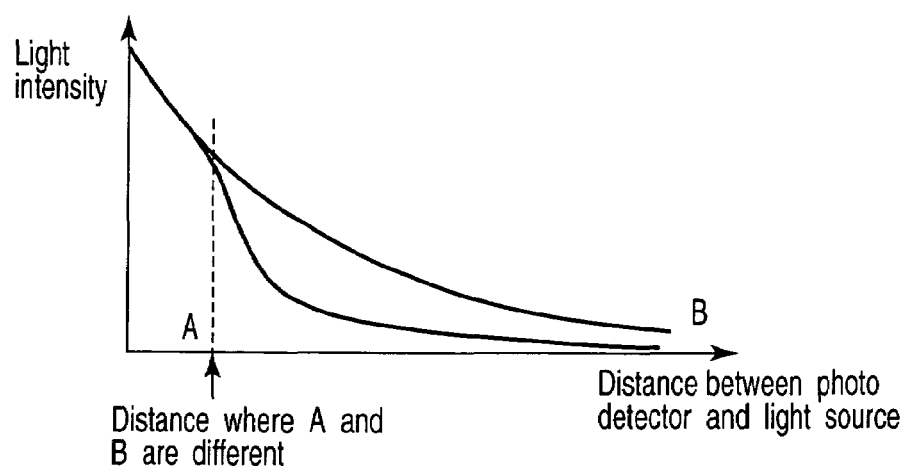
FIG. 8 is a view showing intensity of light obtained by one optical scanning using the present biomedical optical device.

FIG. 8 is a view showing intensity of light obtained by one optical scanning using the wavelength thus selected. In FIG. 8, the axis of abscissas denotes the position of each detector, and the axis of ordinates represents the intensity of light acquired in the time width set in each detector. Curve A shows a case in which the absorber exists beneath the skin, and curve B shows a case of absence thereof. Curve A and curve B coincide in position near the skin, but deviation occurs from the depth in which the absorber exists, and the value of A is smaller than the value of B. This is because the light is absorbed by the absorber and the intensity of returned light is decreased. From the position of the detector, the depth of the absorber existing under the light source can be converted.

Information in the case where the absorber does not exists beneath the skin (information of curve B in the example above) must be acquired preliminarily. This information can be measured, for example, in a model sample, or may be calculated using known optical constants. It is also possible to measure at a position anatomically known to be free from absorber.

Figure 9:
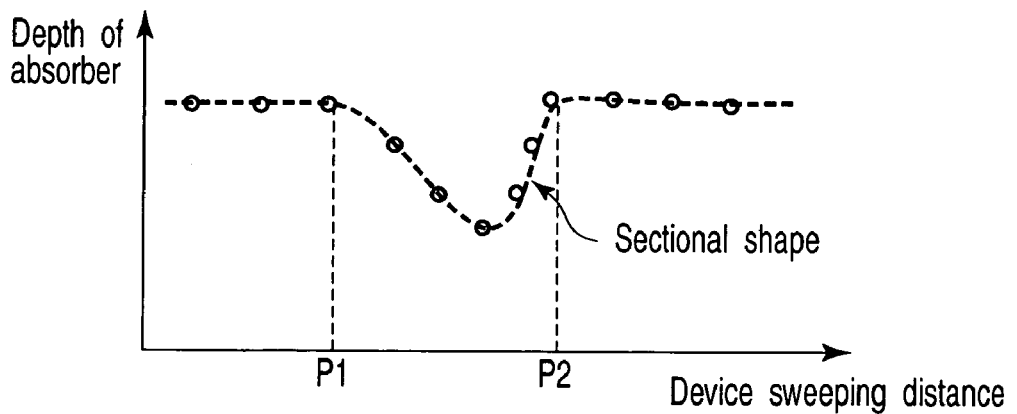
FIG. 9 is a view showing an example of results obtained by optical scanning at each position while moving the biomedical optical device 1.
Figure 10:
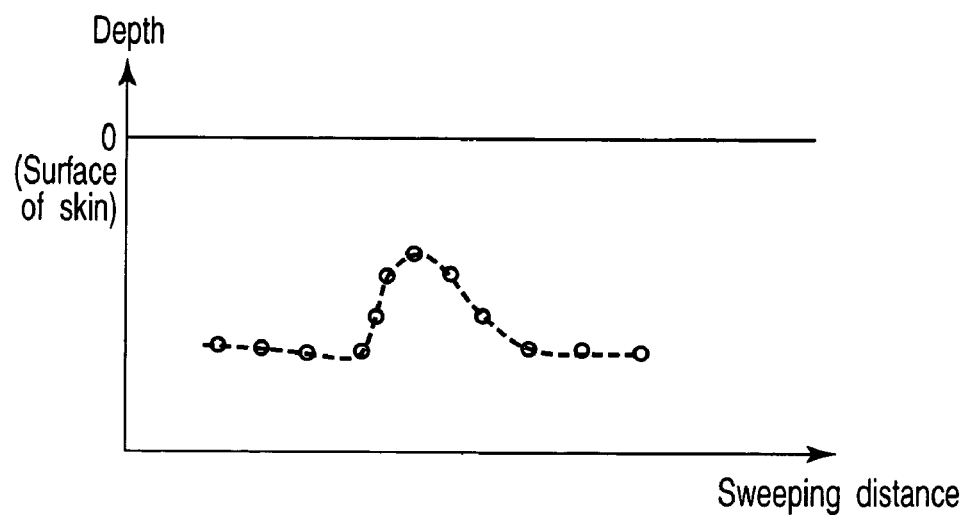
FIG. 10 is a sectional view reconstructed on the basis of data at each detecting position obtained by the biomedical optical device 1.

The biomedical optical device 1 is moved by a predetermined distance along the moving direction shown in FIG. 2, the light intensity distribution is measured again at the moved position, and the depth of the absorber is converted from the position deviated from the curve in the case of presence of the absorber. This operation is repeated while moving the biomedical optical device 1, and results are shown in FIG. 9. The axis of abscissas denotes the device sweeping distance (distance in the moving direction on the arm), and the axis of ordinates represents the depth of the absorber measured from the skin. As shown in FIG. 9, the depth of the absorber becomes deeper from position $P_1$ to position $P_2$. Consequently, it is known that the target object is present between the positions $P_1$ and $P_2$. On the basis of FIG. 9, it is possible to reconstruct a tomographic image with the skin surface as shown in FIG. 10 as a reference.

According to the technique explained herein, the detecting element detected the light reflected by the target object or propagated through the target object is specified by comparing the intensity of light detected by each detecting element when the target object is not present in the illuminated region, and the intensity of light detected by each detecting element when the target object is present in the illuminated region. On the basis of the distance between thus specified detecting element and the light irradiating unit 102, the depth of the target object can be calculated on the basis of the location of the light irradiating unit 102. Also according to this technique, the sectional shape of the absorber can be acquired by sweeping the biomedical optical device 1.

(Operation)

A measuring operation of the biomedical optical device 1 will be explained.

Figure 11:
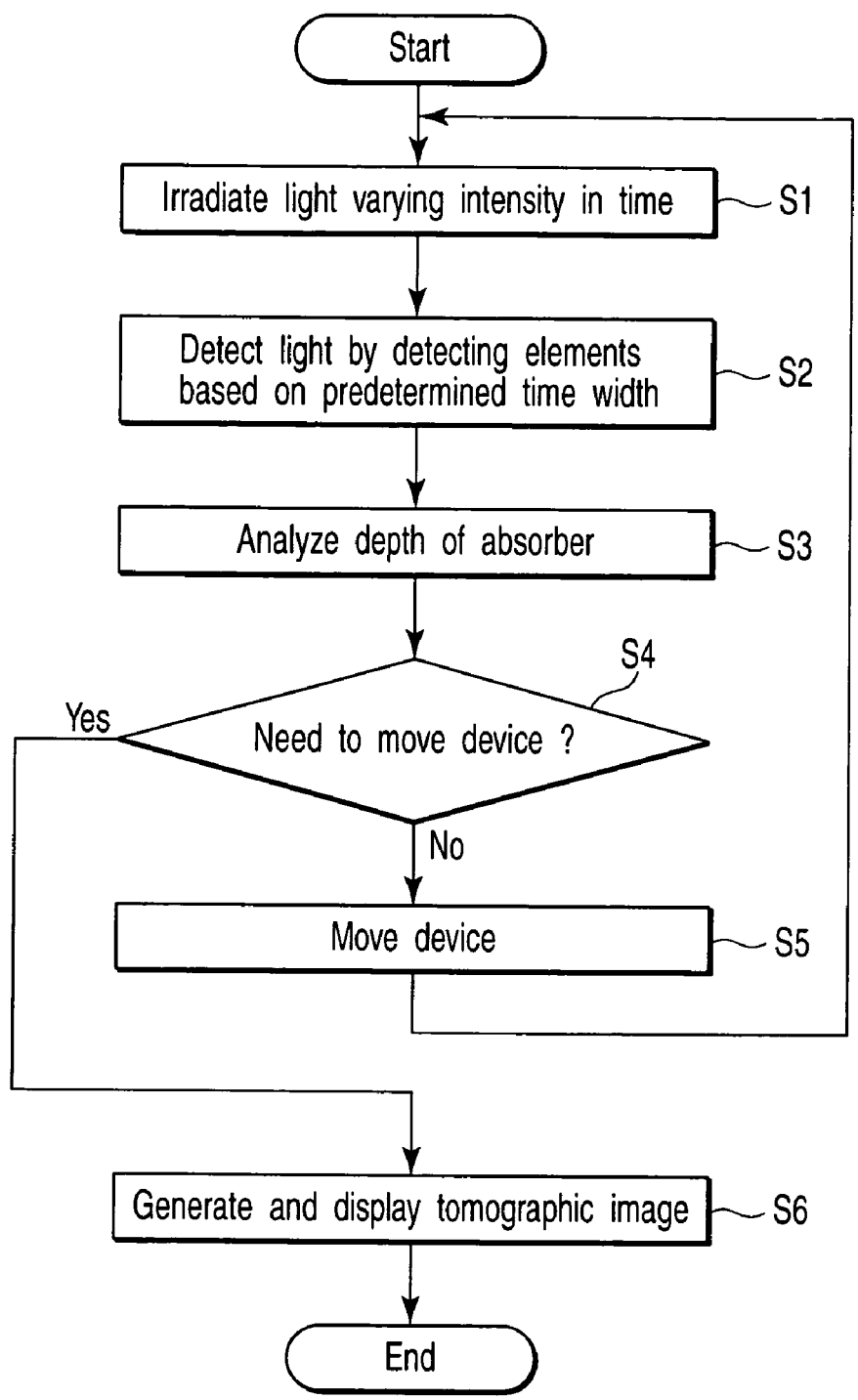
FIG. 11 is a flowchart showing a flow of process to be executed in measurement using the biomedical optical device 1.

FIG. 11 is a flowchart showing a flow of process to be executed in measurement using the biomedical optical device 1. As shown in FIG. 11, light changing in intensity in time is irradiated by the light irradiating unit 102 under the control of the CPU 143 (step S1). On the basis of the time width calculated from the spatial resolution, the detecting element is selected to detect light, only the electrical signal based on the detected light is captured, and the depth of the target object is analyzed (steps S2 and S3). The process in steps S1 to S3 is repeated the predetermined number of times (for example, 1000 times) at the same location of the biomedical optical device.

Next, it is determined whether or not it is necessary to move the device (to change the detecting position) along the moving direction (step S4). If necessary to move, the biomedical optical device is moved to a new position, and the process in steps S1 to S3 is repeated at the moved position (step S5). If not necessary to move, on the other hand, the tomographic image is reconstructed using the depth of the target object obtained at each measuring position, and is displayed in the display unit 18 (step S6).

EXAMPLE

An example of the biomedical optical device 1 will be explained. In this example, the target object is a blood vessel, the absorber is hemoglobin, and the measuring wavelength is 760 nm together with the absorption band of hemoglobin. The light source is a near infrared LED (wavelength 760 nm, output 10 mW), and intensity is modulated at frequency of 500 MHz. The detector is composed of 25 Si photo diodes (fast response), which are linearly arranged along the scanning direction in contact directly with each other to compose a one-dimensional detector.

Numbering the elements sequentially from the light source (1 to 25), the light source is consecutively mounted on the detectors to compose a device (see, for example, FIG. 1). The side of the device contacting with the skin is coated with a silicone rubber thin plate as a buffer material for preventing light scatter and denting in the skin.

A time delay t of a signal measured by detecting elements 1 to 25 is set as follows.

$t = n \times 0.1$ ns (n: detecting element number)

The device is tightly fitted to the inside of the forearm at a position of 5 cm from the elbow, and the longer axis direction is set parallel to the arm (see FIG. 3). The device is placed at a position deviated from the blood vessel and data is collected, and a curve in the absence of the absorber is obtained. Consequently, the device is moved parallel by 3 mm each, and the curve is measured at each position. The curve obtained at each position is compared with the curve measured in the first place, the number of the detector varied in intensity is determined, and the corresponding depth is calculated. Information of the depth thus obtained is plotted at every 3 mm, and the sectional shape of the absorber is acquired.

For reference, the location of the blood vessel inside of the forearm is measured by the inventor by use of an ultrasonic diagnostic apparatus, and is matched with the position of the vein beneath the panniculus adiposus.

By way of comparison, light continuous in time is similarly measured by the inventor without modulating the intensity of the light source. That is, using the signal obtained from each detecting element, a curve in the absence of the absorber is measured, and it is measured whether or not the sectional shape is obtained while moving the position of the device. As a result, when the light is varied in time, a blood vessel in a size of 7 mm is measured, and when consecutive light is used, a size of a blood vessel that can be measured securely is increased, and the depth becomes shallow. This is considered because the spatial resolution is low when measured using the continuous light.

In the configuration mentioned above, the following effects are obtained.

In this biomedical optical device, using a detector having at least two detecting elements arrayed in the scanning direction, optical measurement consecutively changed in light source-detecting position distance can be executed by one optical scan. As a result, conventional discrete data can be improved to consecutive data, and the prior art of distinguishing only two spots, a shallow part and a deep part, is enhanced in resolution in the depth direction up to the state of determining the depth of occurrence of change.

In the biomedical optical device, the detector having at least two detecting elements arrayed in the scanning direction is used, so that it does not require the process of replacing the depth with R as in the conventional spatial resolution method. Therefore, only by fitting the detection surface of a specific size always to the skin, a favorable detection state is assured regardless of the individual physical difference, and more specific information can be obtained by much smaller labor of operation as compared with the prior art.

In the biomedical optical device, moreover, light changing in intensity in time is detected by at least two detecting elements different in distance from a light source, an uptake time delay is varied depending on the difference in distance from the light source. Consequently, the time resolution of the detecting element can be enhanced by the difference in distance, and a higher resolution than in the prior art is realized. As detecting elements, PDs arranged consecutively or CCDs may be used, and unlike the conventional time resolution method, it is not required to use a light source of narrow time width or detecting elements of fast response. In particular, when the conventional time resolution method is employed, for example, to obtain a spatial resolution of 10 mm, the time resolution of sub-nanosecond is needed. According to this device, therefore, the cost of the entire device can be lowered while realizing a high safety as compared with the prior art.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A biomedical optical device comprising:
    a light irradiating unit which is arranged on a surface of a subject, and configure to irradiate light toward a region to be irradiated in the subject, the light with a wavelength to be absorbed by a target object in the subject and intensity varied in time;
    at least two detecting elements which are arrayed at different distances from a location of the light irradiating unit, and which detect the light propagated through the subject;
    a storage unit configure to store the intensity of light detected by each of the detecting elements when the target object is not present in the region to be irradiated;
    a calculating unit which specifies the detecting element detecting the light which was reflected by the target object or propagated through the target object, by comparing the intensity of light detected by each of the detecting elements when the stored target object is not present in the region to be irradiated with the intensity of light detected by each of the detecting elements when the target object is present in the region to be irradiated, and which calculates the depth of the target object by reference to the location of the light irradiating unit on the basis of the distance between the specified detecting element and the light irradiating unit; and
    an output unit which outputs the calculated depth of the target object.

2. The biomedical optical device according to claim 1, further comprising:
    a reconstructing unit which reconstructs a tomographic image on the basis of the calculated at least two depth values of the target object corresponding to at least two different locations of the light irradiating unit,
    wherein the output unit outputs the tomographic image.

3. The biomedical optical device according to claim 1, further comprising: a control unit which controls the detection timing of said each detecting element on the basis of each distance of the light irradiating unit and each of said at least two detecting elements.

4. The biomedical optical device according to claim 3, wherein the control unit delays the detection timing of said each detecting element on the basis of each distance between the light irradiating unit and each of said at least two detecting elements so as to detect a component having a time delay of the light propagated through the subject as departing from the light irradiating unit.

5. The biomedical optical device according to claim 3, wherein the distance between the light irradiating unit and the detecting element closest to the light irradiating unit is 5 mm or less, and when it is assumed that the time until a signal is detected by the detecting element closest to the light irradiating unit is reference time t, the control unit controls the detection timing of said each detecting element so that a time delay from the reference time t is proportional to the distance between the light irradiating unit and the detecting element closest to the light irradiating unit.

6. The biomedical optical device according to claim 1, wherein the light irradiating unit uses near infrared light as the light, and irradiates the light so that a full width at half maximum of light intensity varying with time is 5 nanoseconds or less.

7. The biomedical optical device according to claim 1, wherein said at least two detecting elements are five or more detectors arrayed along one direction departing from the light irradiating unit.

8. The biomedical optical device according to claim 1, wherein said at least two detecting elements are arrayed in a two-dimensional matrix along a first direction departing from the light irradiating unit, and a second direction different from the first direction and departing from the light irradiating unit.

9. A biomedical optical measuring method comprising:
irradiating light toward a region to be irradiated in a subject by a light irradiating unit arranged on the surface of the subject, the light with a wavelength to be absorbed by a target object in the subject and intensity varied in time;
detecting the light propagated through the subject by at least two detecting elements which are arrayed at different distances from a location of the light irradiating unit;
specifying the detecting element detected the light reflected by the target object or propagated through the target object by comparing the intensity of light detected by each of the detecting elements when the stored target object is not present in the region to be irradiated with the intensity of light detected by each of the detecting elements when the target object is present in the region to be irradiated;
calculating the depth of the target object by reference to the location of the light irradiating unit on the basis of the distance between the specified detecting element and the light irradiating unit; and
outputting the calculated depth of the target object.

10. The biomedical optical measuring method according to claim 9, further comprising:
reconstructing a tomographic image on the basis of the calculated at least two depth values of target object corresponding to at least two different locations of the light irradiating unit; and
outputting the tomographic image.

11. The biomedical optical measuring method according to claim 9, further comprising: controlling the detection timing of said each detecting element on the basis of each distance between the light irradiating unit and each of said at least two detecting elements.

12. The biomedical optical measuring method according to claim 11, further comprising: controlling the detection timing of said each detecting element so as to detect a component having a time delay of the light propagated through the subject as departing from the light irradiating unit, by delaying the detection timing of said each detecting element on the basis of each distance between the light irradiating unit and each of said at least two detecting elements.

13. The biomedical optical measuring method according to claim 11, wherein the distance between the light irradiating unit and the detecting element closest to the light irradiating unit is 5 mm or less, the method further comprising:
when it is assumed that the time until a signal is detected by the detecting element closest to the light irradiating unit is reference time t, controlling the detection timing of said each detecting element so that a time delay from the reference time t is proportional to the distance between the light irradiating unit and the detecting element closest to the light irradiating unit.

14. The biomedical optical measuring method according to claim 9, further comprising: using near infrared light as the light and irradiating the light so that a full width at half maximum of light intensity varying with time is 5 nanoseconds or less, by means of the light irradiating unit.

15. The biomedical optical measuring method according to claim 9, wherein said at least two detecting elements are five or more detectors arrayed along one direction departing from the light irradiating unit.

16. The biomedical optical measuring method according to claim 9, wherein said at least two detecting elements are arrayed in a two-dimensional matrix along a first direction departing from the light irradiating unit, and a second direction different from the first direction and departing from the light irradiating unit.

17. A biomedical optical measuring method comprising:
irradiating light toward a region to be irradiated in a subject by a light irradiating unit arranged on the surface of the subject, the light having a wavelength to be absorbed by a target object in the subject and intensity varied in time;
detecting the light propagated through the subject by at least two detecting elements which are arrayed at different distances from the location of the light irradiating unit;
specifying the detecting element detected the light reflected by the target object or propagated through the target object by comparing the intensity of light detected by each of the detecting elements when the stored target object is not present in the region to be irradiated with the intensity of light detected by each of the detecting elements when the target object is present in the region to be irradiated;
calculating the depth of the target object by reference to the location of the light irradiating unit on the basis of the distance between the specified detecting element and the light irradiating unit;
repeating irradiation of the light toward the region to be irradiated, detection of the light propagated through the subject, and calculation of the depth of the target object while moving the light irradiating unit to at least two positions along substantially one direction on the surface of the subject, thereby acquiring the depth of the target object at each of said at least two positions; and
obtaining a tomographic image concerning the target object on the basis of the acquired depth of the target object at each of said at least two positions.

* * * * *